United States Patent [19]

Constantz et al.

[11] Patent Number: 5,782,971
[45] Date of Patent: Jul. 21, 1998

[54] CALCIUM PHOSPHATE CEMENTS COMPRISING AMOROPHOUS CALCIUM PHOSPHATE

[75] Inventors: Brent R. Constantz, Portola Valley; Bryan M. Barr, San Jose, both of Calif.

[73] Assignee: Norian Corporation, Cupertino, Calif.

[21] Appl. No.: 821,021

[22] Filed: Mar. 19, 1997

Related U.S. Application Data

[63] Continuation-in-part of Ser. No. 963,481, Oct. 16, 1992, which is a continuation-in-part of Ser. No. 722,880, Jun. 28, 1991, abandoned.
[51] Int. Cl.$^6$ .............................. C04B 12/02; C01B 25/32
[52] U.S. Cl. .................... 106/690; 106/35; 106/645; 106/691; 423/307; 423/308; 423/311; 423/305; 523/113; 523/116; 523/115; 524/414; 524/436
[58] Field of Search .................. 106/35, 690, 691, 106/462, 645; 501/1; 423/307, 308, 311, 305; 623/16; 433/228.1, 201.1; 523/113, 116, 115; 524/414, 436

[56] References Cited

U.S. PATENT DOCUMENTS

| | | | |
|---|---|---|---|
| Re. 33,161 | 2/1990 | Brown et al. | 423/308 |
| Re. 33,221 | 5/1990 | Brown et al. | 423/308 |
| 4,429,691 | 2/1984 | Niwa et al. | 128/92 |
| 4,518,430 | 5/1985 | Brown et al. | 106/35 |
| 4,612,053 | 9/1986 | Brown et al. | 706/35 |
| 4,684,673 | 8/1987 | Adachi | 523/116 |
| 5,037,639 | 8/1991 | Tung | 424/57 |
| 5,508,342 | 4/1996 | Antonucci et al. | 524/788 |

Primary Examiner—Michael Marcheschi
Attorney, Agent, or Firm—Bozicevic & Reed LLP; Bret E. Field

[57] ABSTRACT

Calcium phosphate cements are provided. The subject cements comprise amorphous calcium phosphate, at least one additional calcium source, usually an additional calcium phosphate, and a liquid component, such as a physiologically acceptable lubricant. Upon combination of the cement components, a flowable composition capable of setting in vivo into a solid calcium phosphate mineral product, such as hydroxyapatite, is produced. The subject cement compositions find use in a variety of applications, including the treatment of injured or compromised hard tissue.

21 Claims, No Drawings

CALCIUM PHOSPHATE CEMENTS COMPRISING AMOROPHOUS CALCIUM PHOSPHATE

CROSS-REFERENCE TO RELATED APPLICATIONS

This application is a continuation-in-part of application Ser. No. 07/963,481 filed on Oct. 16, 1992, which application is a continuation in part of application Ser. No. 07/722,880 filed Jun. 28, 1991, abandoned the disclosures of which are herein incorporated by reference.

INTRODUCTION

1. Technical Field

The technical field of this invention is calcium phosphate cements.

2. Background

Bone is a composite material made up of organic and inorganic components, where the inorganic or mineral phase of bone comprises 60 to 70% of the total dry bone weight. Bone mineral is an apatitic calcium phosphate containing carbonate and small amounts of sodium and magnesium, as well as other trace components. The amount of carbonate present in the mineral phase of bone ranges from about 4 to 6% by weight and this particular carbonated apatite is known as dahllite. In addition to being found in bone, dahllite is also found in teeth and some invertebrate skeletons.

Because bone is naturally subjected to various stresses from which microscopic stress fractures result, all bone tissue is subject to perpetual remodeling, which is a complex process involving a coupled process of bone removal and replacement. At the beginning of the remodeling cycle, osteoclasts erode away bone in targeted areas. In the next phase of the cycle, osteoblasts fill in the osteoclast created cavities with collagen which then mineralizes over several months to become mature bone. The ability of bone to be perpetually remodeled is ascribed, as least in part, to both the calcium phosphate ratio of the mineral phase of bone as well as the particular crystalline nature of bone, as such characteristics provide for the soluble nature of bone and its consequent resorbability.

Under stress, hard tissue is subject to various forms of compromise, such as fracture and compression, which may arise in response to one or more factors, such as breaking of the bone, surgical removal of the bone, destruction or degradation of the bone, bone brittleness and deterioration. In the treatment of compromised hard tissue a number of approaches have been developed, including: the internal and external fixation of fractures, the use of bone cements, e.g. polymethyl methacrylate, the use of ceramic bone filler materials, such as sintered hydroxyapatite, and the like. While each of these approaches has proved useful in certain applications, none of these approaches is entirely satisfactory. For example, hardware used in internal and external fixation methods can pull out of the bone into which it is fastened, causing further damage to the already compromised tissue. While polymethyl methacrylate has been used in a number of diverse applications, it is a foreign material which is not remodelable or remodelable, sets at high temperatures which can result in necrosis of any surrounding tissue, and must be introduced under high pressure.

Because of the above disadvantages associated with current methodologies of hard tissue treatment, there is continued interest in the development of new treatment methodologies. Of particular interest would be the development of a calcium phosphate cement that is capable of setting in vivo into a solid calcium phosphate product which is remodelable and has a crystallinity similar to that of natural bone, where such a cement could be prepared as a flowable paste like composition and then introduced at the hard tissue repair site where it would then set into a solid apatitic product in a clinically relevant period of time.

3. Relevant Literature

Patents and patent applications describing calcium phosphate cements include: U.S. Pat. Nos. 4,880,610; 5,047,031; 5,336,264; 5,569442; RE 33,161; RE 33,221; WO 96/36562; and the like.

References disclosing the use of amorphous calcium phosphate in the preparation of various calcium phosphate comprising compositions include U.S. Pat. Nos. 4,849,193 and 5,037,639, the disclosures of which are herein incorporated by reference. Amorphous calcium phosphate is also described in Phosphate Minerals (1984) Chapter 12, pp. 351–385.

SUMMARY OF THE INVENTION

Calcium phosphate compositions capable of setting in vivo to produce a solid, remodelable phosphate product, as well as methods for their use in the treatment of compromised hard tissue, are provided. The subject compositions comprise amorphous calcium phosphate and at least one additional calcium source, usually at least one additional calcium phosphate source, as well as a physiologically acceptable lubricant. Combination of the various components of the subject compositions produces a flowable, paste-like material capable of setting in vivo into a remodelable calcium phosphate, usually apatitic, product. The subject compositions find use in a variety of applications, particularly in the treatment of compromised hard tissue, such as bone fractures and the like.

DESCRIPTION OF THE SPECIFIC EMBODIMENTS

Flowable calcium phosphate compositions capable of setting in vivo into remodelable calcium phosphate products, and methods for their use in the treatment of compromised hard tissue, are provided. The subject compositions comprise amorphous calcium phosphate, at least one additional calcium source, usually at least one additional calcium phosphate source and physiologically acceptable lubricant. Upon combination of the various components, a flowable, paste like composition is provided which is capable of setting in vivo into a remodelable, usually apatitic product which has a crystallinity that approximates the crystallinity of bone. The subject compositions find a variety of uses, including the treatment of compromised hard tissue, such as bone fractures and the like. In further describing the subject invention, first the subject amorphous calcium phosphates will be described in greater detail, followed by a more detailed description of hydraulic calcium phosphate cements comprising the subject amorphous calcium phosphates and a discussion of methods for their preparation and use.

The amorphous calcium phosphate (ACP) of the subject invention may be either solid or colloidal/gel like compositions. The solid ACP compositions will generally be characterized as precipitated particles, where the particle size will range from 1 to 250 µm, usually from 2 to 100 µm and more usually from 5 to 50 µm, with the shape of the particles being irregular. For the gel ACP, the gel will typically have a density of less than about 1.5 g/cm³, usually less than about 1.25 g/cm$^3$. The molar ratio of calcium to phosphate in the subject ACP compositions will generally range from about 1.5 to 1.8, usually from about 1.6 to 1.7 and more usually from about 1.63 to 1.68.

The subject ACP compositions may be prepared in any convenient manner. Conveniently, calcium and phosphate source solutions may be employed. For the calcium source solution, a solution of a water soluble calcium salt, e.g. calcium chloride or calcium nitrate, the salt usually being other than a phosphate, will be used. For the phosphate source solution, a solution of a water soluble phosphate salt, such as alkali metal phosphates, may be employed. By appropriate choice of ratios and concentrations, one can obtain different compositions which will vary the setting time and ultimate strength of the final product. By appropriate choice of parameters, one can vary the precipitate mineralogies and the pH values of the resultant ACP and cements in which it is employed. The ratio of calcium to phosphate upon combination of the two sources will generally be about 1.5 to 1.8, more usually about 1.6 to 1.7, and particularly about 1.67, as described above.

For the calcium source solution, one or more different soluble calcium salts may be employed, such as calcium chloride, calcium nitrate and the like. The molality of the calcium solution will generally range from about 0.35 to 0.75, more usually from about 0.5 to 0.675.

As for the solution source of phosphate, one or more alkali metal phosphates may be employed, such as sodium phosphate dibasic heptahydrate and sodium phosphate tribasic dodecahydrate. Various ratios of these phosphates may be employed. Generally, the molality of the phosphate solution will range from about 0.2 to 0.5, usually from about 0.3 to 0.4.

To prepare the colloid or gel ACP, solutions of the appropriate molality and volume are prepared and then combined. For the preparation of solid ACP, e.g. ACP crystals, a phosphate solution at an appropriate concentration, as described above, and a pH ranging from about 10–12, usually about 11.5 is employed. The calcium solution is prepared and the two solutions are pumped independently with stirring at a moderate rate, the reaction time requiring about 1 to 4 minutes/liter of reaction mixture. Control of the rate is required to ensure that appropriate sized crystals are obtained. It is found that the precipitate composition will vary from the concentration of the ions in solution. For example, with a calcium/phosphate ratio of 1.67 in solution, the precipitate will have a ratio of about 1.35 to 1.45, resulting in an "octacalcium/hydroxyapatite" ACP product. After the addition of the two solutions is complete and the mixture is allowed to settle, some of the water may be removed from the mixture. Generally, settling will take at least about 10 min and not more than about 60 min. One then mechanically separates the calcium phosphate from the liquid by any convenient means, e.g. centrifugation. The pH of the precipitate should be in the range of about 3.5 to 4.5.

The mixture is centrifuged at between about 3,000 to 6,000 rpm at a temperature of from about 5° to 25° C. After decanting of the supernatant, the gel is vigorously washed with deionized water, usually with at least about 2 to 10 volumes, based on the volume of the gel and the mixture centrifuged. The dispersing and separation is carried out at least once, and preferably at least about three times. The final centrifuging should ensure that substantially all of the calcium phosphate is precipitated to the bottom.

The supernatant is removed from the gel and the gel lyophilized. The resulting powder may then be ground to ensure that all particles are less than about 100 µ. Larger particles may be ground to permit them to pass through the appropriate sieve. The ACP particles are now ready for adding to the calcium phosphate mineral formulation.

The ACP comprising cements of the subject invention generally comprise both a dry component and a liquid component, where the constituent ingredients of the dry component may be premixed prior to combination with the liquid component, where depending on the physical nature of the ACP, it may be present in the dry components or the liquid components, as convenient.

In addition to the ACP, the subject cements will further comprise at least one additional source of calcium. Suitable calcium sources include calcium carbonate, calcium oxide, calcium hydroxide, calcium halide, e.g. calcium fluoride, and the like, as well as calcium phosphates, such as tetracalcium phosphate, tricalcium phosphate, dicalcium phosphate and its dihydrate, monocalcium phosphate and its monohydrate, and the like, where such additional calcium sources may act as bases, acids, sources of counterions and the like, depending on the precise nature of the calcium source.

Thus, depending on the exact nature of the additional calcium source and the function it serves in the cement, the amount of the particular calcium source in the cement will vary. In cements where calcium oxide and/or calcium hydroxide are present, the total amount of one or both of these calcium sources in the cement will usually not exceed 50 weight percent of the composition, and more usually will not exceed 30 weight percent of the compositions, and typically will range from about 5 to 15 weight percent of the composition.

Where calcium carbonate is present as a calcium source, the calcium carbonate will usually be present in an amount ranging from about 0 to 70 weight percent, usually from about 0 to 40 weight percent and more usually from about 2 to 18 weight %.

Where tetracalcium phosphate is present in the subject cements, it will generally be present in an amount ranging from about 55 to 75 weight %, more usually from about 60 to 70 weight % of the weight of the dry components of the cement.

In cements comprising tricalcium phosphate, the amount of tricalcium phosphate will generally range from about 50 to 90 weight %, usually from about 60 to 85 weight %, and more usually 70 to 85 weight % of the dry ingredients.

Meanwhile, for monocalcium phosphate monohydrate (MCPM) which may serve as a phosphoric acid source, the amount of MPCM in the composition, when present, will generally range from about 1 to 35 weight %, usually from about 1 to 25 weight %.

In addition to the calcium source, the subject cements may further comprise an acidic phosphate source. Generally, the acidic phosphate source will be free of uncombined water and may be orthophosphoric acid crystals or MCPM, as described above, or another calcium phosphate acid source by itself or in combination, e.g. monetite. When present, the acidic phosphate source will range from about 15 to 35 weight percent, more usually from about 15 to 25 weight percent.

The ACP component, when employed as a dry, solid component, will typically be combined with the other dry components prior to combination with the liquid component, described in greater detail below. The amount of solid ACP component will generally be sufficient to provide for the desired properties of the cement, usually being present in at least about 5 weight percent, and often less than about 20 weight percent, more often less than about 15 weight percent of the dry ingredients.

The ratio of calcium to phosphate of the entire dry ingredients will provide for stoichiometries ranging from 1.1:1 to 2: 1, allowing preferential formation of a number of stable compounds, including monetite, brushite, octacalcium phosphate, calcium deficient hydroxyapatite, stoichiometric hydroxyapatite or composites thereof, in addition to various metastable amorphous calcium phosphates.

Typically the dry ingredients are combined prior to combination with the liquid component, as described in greater detail below. The dry ingredients will generally be combined into a dry component comprising a powder in which the particle size is generally smaller than about 500 μ, usually smaller than about 250 μ, where the particles typically range in size from about 50 Å to 200 μ on the average. Since small amounts of fine powder will skew the average size, it should be understood that in referring to the average size, the intent is those particles contributing to at least about 80 weight percent of the component, usually at least about 90 weight percent. The mixing of the dry components may occur in any convenient fashion. In some cases, it may be desirable to carry out mixing under conditions such that partial reaction of the dry components occurs, as described in U.S. Pat. Nos. 5,053,212 and 5,178,845, the disclosures of which are herein incorporated by reference.

The liquid component of the subject cement compositions will be a physiologically acceptable lubricant, conveniently an aqueous lubricant, e.g. sterile water. The water which is used will be substantially pure, such as double distilled, deionized or an equivalent thereof. Other hydroxylic materials which are water miscible, pharmacologically acceptable and do not interfere with the calcium mineral formation, may also find use. For example, polyols, such as ethylene glycol, propylene glycol or glycerol may find use in minor amounts, less than about 10 volume percent. All or a portion of the liquid component may comprise the gel or colloid ACP, as described above, where the amount of gel or colloid ACP employed will not exceed 2%, usually less than 1% more and usually less than 0.1%, but at least about 0.01%, where such percentages are based on the dry weight of the colloid as compared to the total weight of the dry components of the cement.

The amount of liquid component that is employed will generally be from about 15 to 70 weight percent, usually from about 25 to 45 weight percent of the entire composition. Preferably, lower amounts of lubricant are used to provide for higher compressive strength and accompanying mechanical properties. The amount of lubricant which is used will be calculated in relation to the amount of water which is formed by reaction of the dry ingredients, so that in referring to the total amount of lubricant, this will include the water produced by the reaction, as well as the lubricant added to the mixture.

In addition to the dry and liquid components as described above, the subject cement compositions may comprise a number of additional ingredients which provide desirable properties to the final cement, where such additional ingredients may be present in the dry and/or liquid components. Such additional ingredients or agents include: organic polymers, e.g. proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g. NaCl, calcium sulfate; sugars, e.g. sucrose, fructose and glucose; pharmaceutically active agents, e.g. antibiotics; and the like, as described in U.S. application Ser. No. 07/722,880, now abandoned, the disclosure of which is herein incorporated by reference.

In using the subject cements, the dry ingredients, which may be premixed into a dry component, will be combined with the liquid component to produce a flowable, biocompatible, usually bioremodelable composition capable of setting into a solid calcium phosphate mineral, e.g. solid apatitic product such as hydroxyapatite, in the presence of large amounts of liquid, e.g. blood. By remodelable is meant that the composition is resorbed by the body in anywhere from 2 weeks to 48 months, depending on the exact nature of the composition, and replaced with natural bone.

The dry ingredients and the wet lubricating medium are combined and thoroughly mixed, so as to provide for a substantially uniform dispersion of the dry ingredients in the lubricant. Once the mixture is uniformly dispersed, it may then be mechanically dispersed, by kneading, rolling, sonicating, or the like. During the mixing, any gas which is formed should be released and the product may be shaped into any appropriate form. The mixing with the lubricant is over a relatively short time, usually not less than about 0.5 minutes and not more than about 5.0 min, usually not more than about 3.0 min. The viscosity of the resultant product may be varied depending on the application. By varying the product composition, percentage of solids, and presence of other additives, the viscosity may be selected to allow for ease of administration to the site to be treated. Where the product is to be introduced in situ, it may be injected into the appropriate site, which may be actively bleeding, using a syringe or catheter, or packed in by other means, as appropriate.

The product is now allowed to set, during which time crystals grow and the product becomes a single integral mass. While the product may harden almost immediately, usually the maturing process should take at least about 2 min, usually about 8 min and not more than about 30 min, usually not more than about 25 min. Alternatively, where the material has been introduced at a site where it is to be retained, the material will naturally harden over time. When desired, very high compressive strengths may be achieved, usually in excess of 5000 psi (35 MPa), preferably in excess of 10,000 psi (75 MPa) and optimally in excess of 15,000 psi (110 MPa).–95% of the final compressive strengths may be substantially achieved within fewer than about 8 hours, preferably fewer than about 4 hours. Time to one-half of the final compressive strength may be fewer than 5 hours, preferably fewer than 3 hours.

The subject calcium phosphate cements may be used for a variety of purposes, such as any form of connective tissue replacement, including bone cement, an injected prosthetic implant, a prosthetic orthopaedic or dental implant, as a root canal filler, a prophylactic injection to augment weak osteoporotic bone, to fill voids resulting from fracture reduction, or a vehicle for drug delivery. The composition may be used as a paste, being applied to a surface for adherence or holding some structure in place. For example, the cement composition may be used to fixate prosthetic devices into regions of bone, as a means of bonding fracture bone fragments together, and the like.

The subject cements may be provided in kit form, in which the dry and liquid components, are provided in various separate containers, e.g. at least one container for dry components and another container for liquid components. For example, the dry components including solid ACP may be provided in one container and the liquid components, e.g. water, may be provided in another container. The kit may further comprise a means for combining the solid and liquid components, such as a mortar and pestle, and the like.

The following examples are offered by way of illustration and not by way of limitation.

EXPERIMENTAL

I. Preparation of Amorphous Calcium Phosphate

A. Powder

Into 10 liters of water is dissolved 80.42 g of sodium dibasic phosphate heptahydrate and 114.03 g of sodium tribasic phosphate dodecahydrate. Into 10 liters of deionized water is dissolved 147.02 g of calcium chloride dihydrate. The pH of the sodium phosphate solution should be about 11.5 The two solutions are then pumped at a rate of about 350 m/min into a reactor with stirring. After the addition of at least one of the reactants has been completed, stirring is ended and the precipitant allowed to settle for about 15 min. Excess water is pumped off the top, leaving about 12 liters of solution and precipitant, which composition is then mixed to uniformly disperse the precipitant. The pH of the medium should be about 3.5–4.5. The dispersion is then centrifuged in 1 liter centrifuge bottles at 4100 rpm at about 10° C. for 5 min. At the end of this time, the supernatant is decanted and the 1 liter centrifuge bottles filled to about the neck with water and vigorously shaken until the calcium phosphate material is substantially dispersed. This process is repeated at least three times, the last centrifugation being performed for 15 min.

The resultant gel is then removed and placed in lyophilizer bottles, placing the gel around the sides of the bottles to prevent a bottle breaking during freezing and to maximize bulk surface area. The gel is then lyophilized. The resulting lyophilized powder is then sieved on a 75 µ screen with large particles being ground to reduce the size of the particles. The particles are now ready for use with the calcium phosphate mineral composition.

B. Gel

A 0.30M sodium phosphate solution is prepared by combining 0.5704 g of trisodium phosphate dodecahydrate and 0.04024 g of dibasic sodium phosphate heptahydrate and dissolved in deionized water to provide the proper molarity. A 0.50M calcium chloride solution is prepared by dissolving 0.0736 g of calcium chloride dihydrate in the appropriate amount of deionized water and the mixture stirred for 15 min. Upon combination of the solutions, an ACP colloid composition is produced.

II. Use Of Amorphous Calcium Phosphate In Hydraulic Calcium Phosphate Cements

A. Teflon mold rings are washed with bovine serum, pH 6.8–7.2. Three centrifuge caps are filled with bovine serum. A formulation (Cement A) comprising 0.2 g $CaCO_3$, 2.11 g $Ca_4(PO_4)_2O$, 0.27 g of ACP as produced in Example I.A., and 0.36 g $H_3PO_4$ (s) is employed. The base and calcium apatite are combined and ground in a mortar for 2–3 sec. Acid is ground into the base mixture for 30 seconds. 2.1 cc deionized water is then added to the mixture and mixed for 2 minutes to form a paste. A 3 cc syringe is filled with the mortar contents for transfer to the Teflon ring molds, which are filled completely. The material is smoothed over with a stainless steel spatula and each filled mold is placed into a cap filled with 1.5 ml of room temperature bovine serum. The caps are then placed in an incubator where the termination of the mixing and introduction into the incubator is less then about 2 min. The pH of the first mold is then determined after 8 min, which should be about 6.8–7, each mold is turned upside down at specified time intervals, after which the probe is gently lowered to the test surface. The probe is allowed to rest on the test surface for approximately 1–2 sec and the probe gently lifted. The surface of the test area is inspected for indentations, where the absence of an indentation indicates the product has set. The process is then repeated with the second and third molds. The last mold is used for mineralogic analysis after 24 h in bovine serum at 37° C., 100% RH.

Various samples are prepared where setting time is determined for a control (no seeding), seeding with a commercially available find hydroxyapatite powder (Baker), colloidal gel prepared as described above, and precipitated calcium phosphate seed prepared as described above, where various concentrations of phosphate and calcium are indicated. The results are provide in Table 1 below under Section III.

B. Into a mortar is introduced 8.60 g of milled base comprising 222.02 g $Ca_4(PO_4)_2O$, 0.85 g of calcium oxide, and 27.13 g $CaCO_3$ (Cement B). After grinding for 15 sec, 1.40 g $H_3PO_4$ are added and ground for 30 seconds. 5.0 g of Example I.B ACP colloid are added and the mixture vigorously agitated with a pestle for 3 min. The paste is scraped from side of the pestle with a spatula to maintain the mixture in the center. The mixture is then ready for use.

III. Measurement Of Setting Times and Compression Strength

A. Setting times were measured as described above. For measurement of compression strength, a compression die is coated with bovine serum and then packed with the test material. Packing may be achieved by finger packing, where the material is introduced into a cavity until the cavity is full, the material compacted with firm finger pressure and the cavity overfilled generously. In the case of a custom constant force spring-loader indention tester (grayometer), the material is inserted into all the cavities by any convenient means, and the material overfilled generously. The material is then smoothed over the top of the die until the material protrudes through the underside by at least 1 mm. The material is then cured while submerged in bovine serum in a plastic bag, where the bag is substantially freed of air. The sealed bag is then placed in a warm bucket of water in an incubator at 37° C. and allowed to set.

The die is removed from the water bath approximately 30 min prior to testing and the die rinsed generously with deionized water. The ends of the compression samples are then shaved to provide flush ends and the samples extracted from the old employing a Delrin® plunger.

An Instron press is employed with appropriate recording charts. The first sample is placed on the platen and testing begun. The test is terminated just as the load starts to drop. Average compression strength is determined by the maximum pressure divided by cross-sectional area.

Various samples are prepared where setting time is determined for a control (no seeding), seeding with a commercially available fine hydroxyapatite powder (Baker), precipitated calcium phosphate seed prepared as described in I.A. and colloidal gel prepared as described above in I.B, where various concentrations of phosphate and calcium are indicated. The results are provide in Tables 1 and 2 below.

TABLE 1

| Additive | Set Time (Min.) | Comp. Strength $\sigma_{max}$ (MPa) |
| --- | --- | --- |
| None | 14 | 23, 21, 21 |
| Baker HA | 18 | |
| ACP of I.A. | 6 | |
| Colloid Gel ACP with PO$_4$ M/Ca M of .42/.7 | 10 | |
| Colloid Gel ACP with PO$_4$ M/Ca M of .36/.6 | 6 | 22, 17, 26 |
| Colloid Gel ACP with PO$_4$ M/Ca M of .30/.5 | 10 | 25 |
| Colloid Gel ACP with PO$_4$ M/Ca M of .24/.4 | 12 | |
| Colloid Gel ACP with PO$_4$ M/Ca M of .06/.1 | 14 | |

TABLE 2

| | Mean Strength (MPa)† | | |
| --- | --- | --- | --- |
| Additive | 1 hr | 4 hr | 24 hr |
| none | 24 | 34 | 35 |
| Baker HA | 21 | 27 | 26 |
| ACP of I.A | 16 | 27 | 18 |
| Colloid Gel ACP with PO$_4$ M/Ca M of .30/.5 | 23 | 31 | 32 |

†Average of 7 values

It is evident from the above results that one can substantially enhance setting times and provide for high compressive strength products as appropriate, by adding calcium phosphate compositions varying from colloidal prepared calcium phosphate minerals for various physiological purposes, where the products set up without significant deterioration from the presence of the blood during the procedure. In this manner, one can introduce strong, relatively long lived structures into the body to provide the necessary stability and support required for fillers, prosthetic devices and the like.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A calcium phosphate cement composition comprising:
   an amorphous calcium phosphate having a calcium to phosphate molar ratio of about 1.6 to 1.8;
   at least one additional calcium source; and
   a physiologically acceptable aqueous liquid.

2. The calcium phosphate cement composition according to claim 1 wherein said at least one additional calcium source is a calcium source selected from calcium oxide, calcium hydroxide, calcium carbonate or calcium phosphate.

3. The calcium phosphate cement composition according to claim 2, wherein said calcium phosphate of said at least one additional calcium source is selected from the group consisting of tetracalcium phosphate, tricalcium phosphate and monocalcium phosphate monohydrate.

4. The calcium phosphate cement composition according to claim 2, wherein said amorphous calcium phosphate is a solid.

5. The calcium phosphate cement composition according to claim 2, wherein said amorphous calcium phosphate is a gel.

6. The calcium phosphate cement composition according to claim 5, wherein said gel consists of said amorphous calcium phosphate and said physiologically acceptable liquid.

7. A calcium phosphate cement composition comprising:
   (a) a dry component comprising an amorphous calcium phosphate having a calcium to phosphate molar ratio of about 1.6 to 1.8 and at least one additional calcium phosphate; and
   (b) a physiologically acceptable aqueous lubricant.

8. The calcium phosphate cement composition according to claim 7, wherein said at least one additional calcium phosphate is selected from the group consisting of tetracalcium phosphate, tricalcium phosphate and monocalcium phosphate monohydrate.

9. The calcium phosphate cement composition according to claim 8, wherein said cement further comprises an organic polymer.

10. The calcium phosphate cement composition according to claim 9, wherein said organic polymer is a protein.

11. A method for preparing a remodelable calcium phosphate mineral, said method comprising:
    combining (a) an amorphous calcium phosphate having a calcium to phosphate molar ratio of about 1.6 to 1.8, (b) at least one additional calcium source and (c) a physiologically acceptable aqueous lubricant to produce a flowable composition; and
    allowing said flowable composition to set into said calcium phosphate mineral.

12. The method according to claim 11, wherein said at least one additional calcium source is selected from the group consisting of calcium oxide, calcium hydroxide, calcium carbonate and calcium phosphate.

13. The method according to claim 12, wherein said calcium phosphate of said at least one additional calcium source is selected from the group consisting of tetracailcium phosphate, tricalcium phosphate and monocalcium phosphate monohydrate.

14. The method according to claim 11, wherein said calcium phosphate mineral is an apatite.

15. The method according to claim 14, wherein said apatite is hydroxyapatite.

16. The method according to claim 15, wherein said hydroxyapatite is calcium deficient hydroxyapatite.

17. A method for preparing a remodelable hydroxyapatite, said method comprising:
    combining (a) a dry component comprising an amorphous calcium phosphate having a calcium to phosphate molar ratio of about 1.6 to 1.8 and at least one additional calcium phosphate with (b) physiologically acceptable aqueous lubricant to produce a flowable composition; and
    allowing said flowable composition to set into said remodelable hydroxyapatite.

18. The method according to claim 17, wherein said remodelable hydroxyapatite is calcium deficient hydroxyapatite.

19. The method according to claim 18, wherein said at least one additional calcium phosphate is tetracalcium phosphate.

20. The method according to claim 18, wherein said at least one additional calcium phosphate is tricalcium phosphate.

21. A kit comprising the cement according to claim 1.

* * * * *

REEXAMINATION CERTIFICATE (3880th)

United States Patent [19]
Constantz et al.

[11] B1 5,782,971
[45] Certificate Issued: Sep. 21, 1999

[54] CALCIUM PHOSPHATE CEMENTS COMPRISING AMOROPHOUS CALCIUM PHOSPHATE

[75] Inventors: Brent R. Constantz, Portola Valley; Bryan M. Barr, San Jose, both of Calif.

[73] Assignee: Norian Corporation, Cupertino, Calif.

Reexamination Request:
No. 90/005,121, Sep. 28, 1998

Reexamination Certificate for:
Patent No.: 5,782,971
Issued: Jul. 21, 1998
Appl. No.: 08/821,021
Filed: Mar. 19, 1997

Related U.S. Application Data

[63] Continuation-in-part of application No. 07/963,481, Oct. 16, 1992, which is a continuation-in-part of application No. 07/722,880, Jun. 28, 1991, abandoned.

[51] Int. Cl.$^6$ ............................ C04B 12/02; C01B 25/32
[52] U.S. Cl. ............................ 106/690; 106/35; 106/645; 106/691; 423/307; 423/308; 423/311; 423/305; 523/113; 523/116; 523/115; 524/414; 524/436

[58] Field of Search ...................................... 106/690, 645, 106/691, 35; 423/308, 311, 307, 305; 524/2, 414, 436; 523/113, 116, 115

[56] References Cited

U.S. PATENT DOCUMENTS

| | | | |
|---|---|---|---|
| 5,650,176 | 7/1997 | Lee et al. | 424/602 |
| 5,676,976 | 10/1997 | Lee | 424/602 |
| 5,683,461 | 11/1997 | Lee et al. | 623/16 |

FOREIGN PATENT DOCUMENTS

| | | | |
|---|---|---|---|
| WO 96/36562 | 11/1996 | WIPO | C01B 25/32 |

*Primary Examiner*—Michael Marcheschi

[57] ABSTRACT

Calcium phosphate cements are provided. The subject cements comprise amorphous calcium phosphate, at least one additional calcium source, usually an additional calcium phosphate, and a liquid component, such as a physiologically acceptable lubricant. Upon combination of the cement components, a flowable composition capable of setting in vivo into a solid calcium phosphate mineral product, such as hydroxyapatite, is produced. The subject cement compositions find use in a variety of applications, including the treatment of injured or compromised hard tissue.

B1 5,782,971

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–21 is confirmed.

New claims 22–39 are added and determined to be patentable.

22. *A calcium phosphate cement composition comprising:*
   *(a) a calcium phosphate composition having a calcium to phosphate molar ratio of about 1.6 to 1.8 and prepared by: (i) combining a phosphate solution of a soluble phosphate salt and a calcium solution of a soluble calcium salt under stirring conditions; (ii) allowing a precipitate to form; and (iii) drying said precipitate to produce said calcium phosphate;*
   *(b) at least one additional calcium source; and*
   *(c) a physiologically acceptable aqueous liquid.*

23. *The calcium phosphate cement composition according to claim 22, wherein said at least one additional calcium source is a calcium source selected from calcium oxide, calcium hydroxide, calcium carbonate or calcium phosphate.*

24. *The calcium phosphate cement composition according to claim 23, wherein said calcium phosphate of said at least one additional calcium source is selected from the group consisting of tetracalcium phosphate, tricalcium phosphate and monocalcium phosphate monohydrate.*

25. *A calcium phosphate cement composition comprising:*
   *(a) dry component comprising a calcium phosphate having a calcium to phosphate molar ratio of about 1.6 to 1.8, wherein said first calcium phosphate is prepared by (i) combining a phosphate solution of a soluble phosphate salt and a calcium solution of a soluble calcium salt under stirring conditions; (ii) allowing a precipitate to form; and (iii) drying said precipitate to produce said first calcium phosphate; and at least one additional calcium phosphate; and*
   *(b) a physiologically acceptable aqueous lubricant.*

26. *The calcium phosphate cement composition according to claim 25, wherein said at least one additional calcium phosphate is selected from the group consisting of tetracalcium phosphate, tricalcium phosphate and monocalcium phosphate monohydrate.*

27. *The calcium phosphate cement composition according to claim 26, wherein said cement further comprises an organic polymer.*

28. *The calcium phosphate cement composition according to claim 27, wherein said organic polymer is a protein.*

29. *A method for preparing a remodelable calcium phosphate mineral, said method comprising:*
   *combining (a) a calcium phosphate composition having a calcium to phosphate molar ratio of about 1.6 to 1.8, wherein said calcium phosphate composition is prepared by: (i) combining a phosphate solution of a soluble phosphate salt and a calcium solution of a soluble calcium salt under stirring conditions; (ii) allowing a precipitate to form; and (iii) drying said precipitate to produce said calcium phosphate; (b) at least one additional calcium source and (c) a physiologically acceptable aqueous lubricant to produce a flowable composition; and*
   *allowing said flowable compositions to set into said calcium phosphate mineral.*

30. *The method according to claim 29, wherein said at least one additional calcium source is selected from the group consisting of calcium oxide, calcium hydroxide, calcium carbonate and calcium phosphate.*

31. *The method according to claim 30, wherein said calcium phosphate of said at least one additional calcium source is selected from the group consisting of tetracalcium phosphate, tricalcium phosphate and monocalcium phosphate monohydrate.*

32. *The method according to claim 29, wherein said calcium phosphate mineral is an apatite.*

33. *The method according to claim 32, wherein said apatite is hydroxyapatite.*

34. *The method according to claim 33, wherein said hydroxyapatite is calcium deficient hydroxyapatite.*

35. *A method for preparing a remodelable hydroxyapatite, said method comprising:*
   *combining:*
   *(a) a dry component comprising:*
      *a calcium phosphate having a calcium to phosphate molar ratio of about 1.6 to 1.8 and prepared by:*
         *(i) combining a phosphate solution of a soluble phosphate salt and a calcium solution of a soluble calcium salt under stirring conditions;*
         *(ii) allowing a precipitate to form; and*
         *(iii) drying said precipitate to produce said calcium phosphate; and*
      *at least one additional calcium phosphate; and*
   *(b) a physiologically acceptable aqueous lubricant to produce a flowable composition; and*
   *allowing said flowable composition to set into said remodelable hydroxyapatite.*

36. *The method according to claim 35, wherein said remodelable hydroxyapatite is calcium deficient hydroxyapatite.*

37. *The method according to claim 35, wherein said at least one additional calcium phosphte is tetracalcium phosphate.*

38. *The method according to claim 35, wherein said at least one additional calcium phosphate is tricalcium phosphate.*

39. *A kit comprising the cement according to claim 22.*

* * * * *